United States Patent
Serafin, Jr.

(10) Patent No.: US 9,427,322 B1
(45) Date of Patent: Aug. 30, 2016

(54) HIP IMPLANT

(71) Applicant: Louis A. Serafin, Jr., Lakeport, MI (US)

(72) Inventor: Louis A. Serafin, Jr., Lakeport, MI (US)

(73) Assignee: Signal Medical Corporation, Marysville, MI (US)

( * ) Notice: Subject to any disclaimer, the term of this patent is extended or adjusted under 35 U.S.C. 154(b) by 194 days.

(21) Appl. No.: 13/987,015

(22) Filed: Jun. 25, 2013

Related U.S. Application Data

(60) Provisional application No. 61/690,450, filed on Jun. 27, 2012.

(51) Int. Cl.
  *A61F 2/36* (2006.01)
(52) U.S. Cl.
  CPC .................... *A61F 2/3607* (2013.01)
(58) Field of Classification Search
  CPC ............. A61F 2/36–2/3676; A61F 2/3859; A61F 2002/2853; A61F 2002/32; A61F 2002/3662; A61F 2002/3672; A61F 2002/3674; A61F 2002/3684; A61F 2002/3686; A61F 2002/3688
  USPC ........... 623/22.4–22.46, 23.23, 23.24, 23.25, 623/23.26, 23.35
  See application file for complete search history.

(56) References Cited

U.S. PATENT DOCUMENTS

| | | | | |
|---|---|---|---|---|
| 2,719,522 A | * | 10/1955 | Hudack .................. | 623/23.15 |
| 3,859,669 A | * | 1/1975 | Shersher .................. | 623/22.44 |
| 3,925,824 A | * | 12/1975 | Freeman et al. .......... | 623/23.12 |
| 3,965,490 A | * | 6/1976 | Murray et al. ............. | 623/23.29 |
| 4,068,324 A | * | 1/1978 | Townley et al. ........... | 623/23.24 |
| 4,101,985 A | * | 7/1978 | Baumann et al. ......... | 623/22.46 |
| 4,514,865 A | * | 5/1985 | Harris ............... | 606/62 |
| 4,589,883 A | * | 5/1986 | Kenna ........................ | 623/23.35 |
| 4,608,055 A | * | 8/1986 | Morrey et al. ............. | 623/22.46 |
| 4,657,552 A | * | 4/1987 | Karpf ........................ | 623/23.15 |
| 4,661,112 A | * | 4/1987 | Muller ....................... | 623/23.22 |
| 4,695,283 A | * | 9/1987 | Aldinger .................... | 623/23.24 |
| 4,728,335 A | * | 3/1988 | Jurgutis ..................... | 623/23.23 |
| 4,770,661 A | * | 9/1988 | Oh .............................. | 623/22.2 |
| 4,813,963 A | * | 3/1989 | Hori et al. ................ | 623/23.35 |
| 4,865,608 A | * | 9/1989 | Brooker, Jr. ............... | 623/23.29 |
| 4,944,761 A | * | 7/1990 | Stuhmer et al. ........... | 623/23.31 |

(Continued)

OTHER PUBLICATIONS

Serafin, Jr., U.S. Appl. No. 61/690,450, filed Jun. 27, 2012 A.D.

(Continued)

*Primary Examiner* — Alvin Stewart
(74) *Attorney, Agent, or Firm* — Christopher John Rudy

(57) ABSTRACT

Hip implant femoral component includes a stem, say, as a flattened, rounded tapered spike having an upper trunnion with a self-holding taper, which may be symmetrical about the same central axis. A neck—say, as a flattened, curved mass having a lower receptacle with a self-holding taper to receive the stem trunnion, and an upper trunnion with a self-holding taper for holding a ball head with a corresponding receptacle—may be attached. A securing screw for threading into a threaded receptacle of the stem trunnion, which may have a truncated inverse cone head, may be employed to further secure the stem and neck together. The component, especially the stem and neck, or stem, neck and screw, may be made with a nonmagnetic cobalt-chromium-molybdenum alloy exhibiting high strength, wear and corrosion resistance, as a wrought powder metallurgy product, which is essentially if not fully 100% dense.

20 Claims, 1 Drawing Sheet

(56) References Cited

U.S. PATENT DOCUMENTS

| | | | |
|---|---|---|---|
| 4,946,379 A * | 8/1990 | Berchem | 623/23.44 |
| 4,957,510 A * | 9/1990 | Cremascoli | 623/22.46 |
| 5,002,578 A * | 3/1991 | Luman | 623/22.42 |
| 5,047,062 A * | 9/1991 | Pappas et al. | 623/22.4 |
| 5,066,304 A * | 11/1991 | Crowninshield et al. | 623/22.45 |
| 5,080,685 A * | 1/1992 | Bolesky et al. | 623/22.42 |
| 5,116,379 A * | 5/1992 | McLardy-Smith | 623/22.42 |
| 5,163,961 A * | 11/1992 | Harwin | 623/22.46 |
| 5,181,928 A * | 1/1993 | Bolesky et al. | 623/22.42 |
| 5,314,489 A * | 5/1994 | Hoffman et al. | 623/23.25 |
| 5,314,494 A * | 5/1994 | Huiskes et al. | 623/23.35 |
| 5,342,366 A * | 8/1994 | Whiteside et al. | 606/86 R |
| 5,462,575 A | 10/1995 | Del Corso | 75/243 |
| D364,926 S * | 12/1995 | Webb et al. | D24/155 |
| 5,480,453 A * | 1/1996 | Burke | 623/23.21 |
| 5,553,476 A * | 9/1996 | Oehy et al. | 72/325 |
| 5,653,764 A * | 8/1997 | Murphy | 623/23.46 |
| 5,653,765 A * | 8/1997 | McTighe et al. | 623/22.42 |
| 5,755,805 A * | 5/1998 | Whiteside | 623/23.24 |
| 5,755,810 A * | 5/1998 | Cunningham | 623/22.44 |
| 5,824,108 A * | 10/1998 | Huebner | 623/22.29 |
| 5,888,210 A * | 3/1999 | Draenert | 623/23.35 |
| 5,906,644 A * | 5/1999 | Powell | 623/20.15 |
| 5,951,606 A * | 9/1999 | Burke | 623/23.15 |
| 6,013,080 A * | 1/2000 | Khalili | 606/86 R |
| 6,030,417 A * | 2/2000 | Bresler et al. | 623/23.15 |
| 6,200,350 B1 | 3/2001 | Masini | |
| 6,238,436 B1 * | 5/2001 | Lob et al. | 623/22.42 |
| 6,245,112 B1 * | 6/2001 | Doubler et al. | 623/22.41 |
| 6,264,699 B1 * | 7/2001 | Noiles et al. | 623/23.23 |
| 6,306,174 B1 * | 10/2001 | Gie | A61F 2/3609 623/22.42 |
| 6,332,896 B1 * | 12/2001 | Hubbard et al. | 623/23.24 |
| 6,361,566 B1 * | 3/2002 | Al-Hafez | 623/22.15 |
| 6,383,225 B2 * | 5/2002 | Masini | 623/22.42 |
| 6,413,280 B1 * | 7/2002 | Feiler | 623/22.15 |
| 6,428,578 B2 * | 8/2002 | White | 623/23.22 |
| 6,436,147 B1 * | 8/2002 | Zweymuller | 623/22.41 |
| 6,436,148 B1 * | 8/2002 | DeCarlo et al. | 623/23.15 |
| 6,702,854 B1 * | 3/2004 | Cheal et al. | 623/22.42 |
| 6,706,072 B2 * | 3/2004 | Dwyer | A61F 2/30734 606/89 |
| 6,383,225 C1 | 4/2005 | Masini | |
| 6,887,276 B2 * | 5/2005 | Gerbec et al. | 623/18.11 |
| 6,200,350 C1 | 6/2005 | Masini | |
| 6,994,731 B2 * | 2/2006 | Howie | A61F 2/3662 623/23.35 |
| 7,497,875 B1 * | 3/2009 | Zweymuller | 623/23.35 |
| 7,559,950 B2 * | 7/2009 | Keller | 623/23.31 |
| 7,572,297 B2 * | 8/2009 | Cheal et al. | 623/22.43 |
| 7,799,085 B2 * | 9/2010 | Goodfried et al. | 623/20.15 |
| 7,828,805 B2 * | 11/2010 | Hoag et al. | 606/89 |
| 7,854,737 B2 | 12/2010 | Daniels et al. | |
| 7,857,859 B2 * | 12/2010 | Willi | A61F 2/3609 623/22.42 |
| 8,425,618 B2 * | 4/2013 | Caillouette et al. | 623/22.42 |
| 8,529,578 B2 | 9/2013 | Daniels et al. | |
| 8,562,690 B1 * | 10/2013 | Dickerson | 623/22.42 |
| 8,858,646 B2 * | 10/2014 | Fridshtand et al. | 623/23.24 |
| 8,906,108 B2 * | 12/2014 | Armacost | A61F 2/3662 623/18.11 |
| 2001/0008981 A1 * | 7/2001 | Masini | 623/22.42 |
| 2004/0078083 A1 * | 4/2004 | Gibbs et al. | 623/22.17 |
| 2004/0122440 A1 | 6/2004 | Daniels et al. | |
| 2005/0055103 A1 * | 3/2005 | Badatcheff | A61F 2/36 623/22.42 |
| 2006/0217815 A1 * | 9/2006 | Gibbs et al. | 623/22.17 |
| 2007/0050042 A1 * | 3/2007 | Dietz et al. | 623/23.46 |
| 2007/0118229 A1 * | 5/2007 | Bergin et al. | 623/23.31 |
| 2007/0225818 A1 * | 9/2007 | Reubelt et al. | 623/19.12 |
| 2008/0091274 A1 * | 4/2008 | Murphy | A61F 2/3609 623/22.42 |
| 2008/0133023 A1 * | 6/2008 | Schlotterback et al. | 623/22.42 |
| 2008/0200990 A1 * | 8/2008 | McTighe | A61F 2/36 623/22.42 |
| 2008/0243264 A1 * | 10/2008 | Fonte | 623/22.43 |
| 2008/0312749 A1 * | 12/2008 | May et al. | 623/23.35 |
| 2009/0105714 A1 * | 4/2009 | Kozak | 606/102 |
| 2010/0152860 A1 * | 6/2010 | Brooks et al. | 623/22.42 |
| 2011/0009976 A1 * | 1/2011 | Cruchet | 623/22.46 |
| 2011/0032184 A1 * | 2/2011 | Roche et al. | 345/156 |
| 2011/0046745 A1 * | 2/2011 | Daniels et al. | 623/22.42 |
| 2012/0065737 A1 * | 3/2012 | Chow | 623/22.42 |
| 2012/0221115 A1 * | 8/2012 | Komistek | 623/22.15 |
| 2013/0030543 A1 * | 1/2013 | Morrey et al. | 623/22.4 |
| 2013/0158557 A1 * | 6/2013 | Komistek | 606/89 |
| 2013/0158674 A1 * | 6/2013 | Chow et al. | 623/23.26 |
| 2013/0165938 A1 * | 6/2013 | Chow et al. | 606/87 |
| 2013/0304225 A1 * | 11/2013 | Komistek | 623/22.16 |
| 2014/0257510 A1 * | 9/2014 | Gerges et al. | 623/22.42 |

OTHER PUBLICATIONS

Whiteside Biomechanics, Inc., Quatroloc® Femoral System, www.whitesidebio.com, 6 pages, 2002, copied from download Dec. 16, 2009.

Carpenter Technology Corporation, Technical Datasheet, BioDur® CCM Plus® Alloy, 2012 (Jan. 18, 2007 Edition), 4 pages.

Khanna, A., et al., Priory Lodge Education Limited (Priory.com), "Prosthetic femoral stem fracture with intact femur: A missed diagnosis," first published Jun. 2007, printer friendly version printed Jun. 5, 2012, 6 pages.

Record List Display, TESS search (Vitallium)[COMB] Mar. 21, 2015, 13 hits.

Vitallium, Reg. No. 577,389 (Jul. 14, 1953), TESS search Mar. 21, 2015.

Vitallium, Reg. No. 327,489 (Aug. 27, 1935), TESS search Mar. 21, 2015.

* cited by examiner

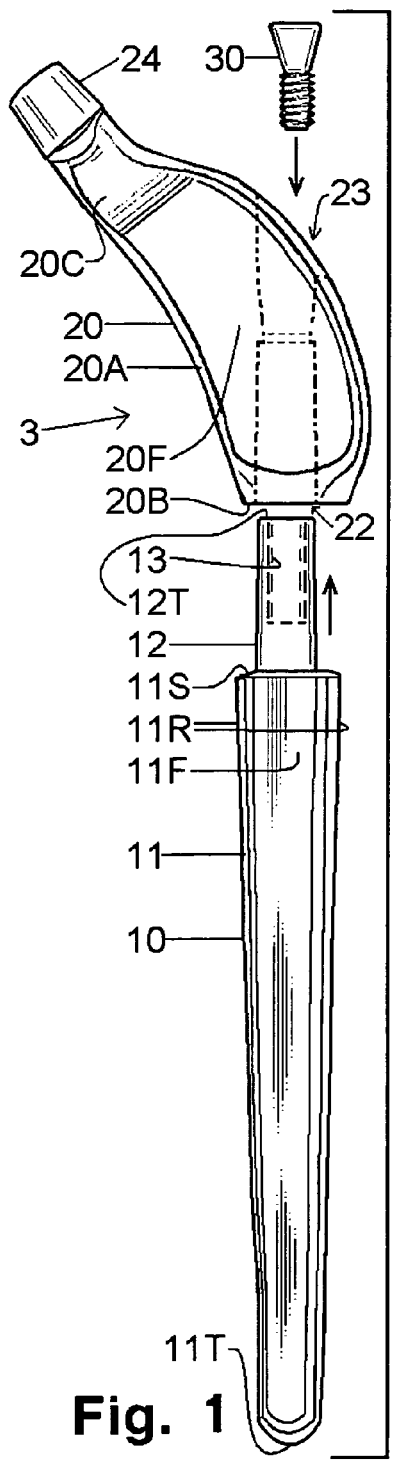
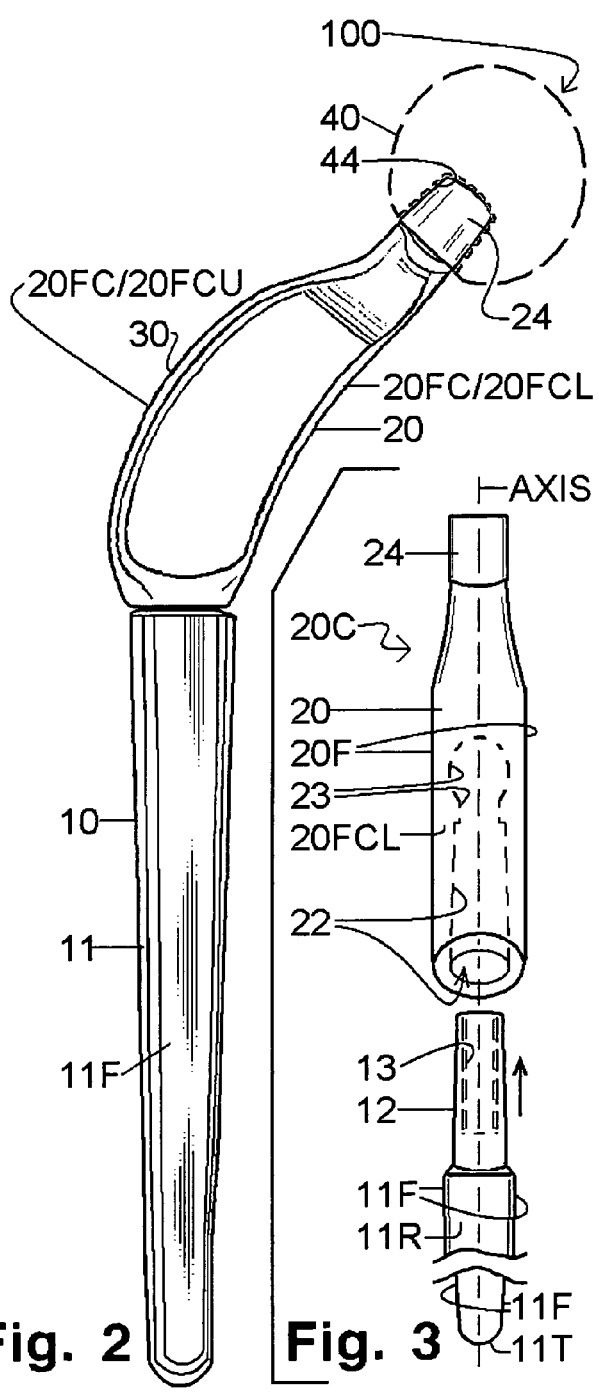
Fig. 1   Fig. 2   Fig. 3

HIP IMPLANT

This claims the benefits under 35 USC 119(e) of provisional patent application No. U.S. 61/690,450 filed on Jun. 27, 2012 A.D. The specification of that application in its entirety, to include its drawings, is incorporated herein by reference.

FIELD OF THE INVENTION

This concerns a hip implant femoral component.

BACKGROUND TO THE INVENTION

A problem in the art is that on occasion, the stem of a hip implant breaks. This is extremely painful, and expensive, with a replacement necessary. See, e.g., A. Khanna et al., Priory.com, "Femoral Fracture," www.priory.com/surgery/Femoral_Fracture.htm.

Carpenter Technology Corporation produces a non-magnetic, cobalt-chromium-molybdenum alloy that exhibits high strength, corrosion resistance, and wear resistance, known as BioDur (Reg. U.S. Pat. & Tm. Off.) CCM Plus (Reg. U.S. Pat. & Tm. Off.) alloy. Compare, U.S. Pat. No. 5,462,575—which is incorporated herein by reference in its entirety. A technical datasheet from Carpenter notes that the alloy is a high carbon version of BioDur Carpenter CCM (Reg. U.S. Pat. & Tm. Off.) alloy and meets the requirements of ASTM F-1537, ASTM F-799, ISO 5832-12 and ISO 5832-4; and that BioDur CCM Plus alloy should be considered as a candidate for use in the orthopedic industry for joint replacement and fracture fixation devices such as total hip, knee, and shoulder replacements, especially when wear or fatigue properties are of major importance or where intricate high strength forgings are required; and for use in producing large forgings where it is difficult to attain ASTM F-799 properties throughout the forging's cross section due to a lack of sufficient thermomechanical processing, with applications having had included hip and knee forgings and machined modular femoral heads for metal-metal and metal-HDPE wear couples.

It would be desirable to ameliorate if not solve the problem of breakage in hip implants, to include in their stems. It would be desirable to provide the art an alternative.

DISCLOSURE OF THE INVENTION

In address of the problem, provided hereby is a hip implant femoral component, which comprises a stem in a particular configuration, say, a flattened, rounded tapered spike having an upper trunnion with a self-holding taper, which may be symmetrical about the same central axis. A neck in a particular configuration—say, a flattened, curved mass having a lower receptacle with a self-holding taper to receive the trunnion of the stem, and an upper trunnion with a self-holding taper to hold a ball head with a corresponding receptacle—may be attached. A securing screw for threading into a threaded receptacle of the trunnion of the stem, and which may have a truncated inverse cone head, may be employed to further secure the stem and neck together. The hip ball head may be provided. The hip implant femoral component, especially the stem and neck, or the stem, neck and screw, may be made, for example, with a nonmagnetic cobalt-chromium-molybdenum alloy exhibiting high strength, wear and corrosion resistance, as a wrought powder metallurgy product, which is essentially if not fully 100% dense, such as disclosed in the fully incorporated U.S. Pat. No. 5,462,575.

The invention is useful in orthopedics.

Significantly, by the invention, the art is advanced in kind, and a viable alternative is provided. In particular, hip implant stem fracture occurrence, and its accompanying fear and pain, as well as expense to the patient, insurance company, surgeon and/or medical device seller or manufacturer can be reduced if not eliminated. Numerous further advantages attend the invention.

The drawings form part of the specification hereof. With respect to the drawings, which are not necessarily drawn to scale, the following is briefly noted:

FIG. 1 is an elevational plan view of a hip implant hereof.

FIG. 2 is a view of the implant of FIG. 1, nearly assembled.

FIG. 3 is a plan view of the implant of FIG. 1 along arrow 3.

The invention can be further understood by the detail set forth below. Such is to be taken in an illustrative, but not necessarily limiting, sense.

As for the hip implant femoral component, it includes a stem that is made with a nonmagnetic cobalt-chromium-molybdenum alloy exhibiting high strength, wear and corrosion resistance, as a wrought powder metallurgy product. Any suitable configuration can be employed. The femoral component can be for a total hip replacement, which would include a complimentary acetabular cup implant component, or it may be for a hemiarthroplasty.

As for the aforesaid BioDur CCM Plus alloy, it may be produced by vacuum induction melting, gas atomization and hot isostatic pressing to make an essentially if not fully 100% dense billet, which can be processed by known steel-making practices for the final product. See, U.S. Pat. No. 5,462,575. Thus, the alloy can be a substantially full dense, powder metallurgy article, from a cobalt-chromium-molybdenum alloy powder having a composition weight percent of about: Carbon 0.35% max.; Manganese, 1.00% max.; Silicon, 1.00% max.; Chromium, 26.0%-30.0%; Molybdenum, 5.0%-7.0%; Nickel; 3.00% max.; Nitrogen, 0.25% max.; Iron, 1.00% max.; Oxide Forming Metals, 0.01.% max.; Cobalt, balance—wherein the amounts of carbon and nitrogen in the alloy satisfy the relationship: $62.866 + 360.93 \times (\% \text{ Carbon}) + 286{,}633 \times (\% \text{ Nitrogen}) - 682.165 \times (\% \text{ Carbon})^2 - 641.702 \times (\% \text{ Nitrogen})^2$ is greater than or equal to 120. The alloy can be commercially obtained, for example, as BioDur CCM Plus alloy from Carpenter, which can have the following type analysis:

| Cobalt | All but the following, i.e., balance of: | | |
|---|---|---|---|
| Chromium | 26.00 to 30.00% | Carbon | 0.20 to 0.30% |
| Molybdenum | 5.00 to 7.00% | Nitrogen | 0.15 to 0.20%. |

With reference to the drawings, hip implant femoral component 100 includes one-piece stem 10 of the aforesaid alloy, which includes distal portion 11, which can have opposing flat faces 11F that blend into opposing convexly rounded faces 11R, shoulder 11S, and rounded tip 11T. The flat faces 11F can be in a form of a truncated slight V-shape when viewed generally perpendicular to the rounded faces 11R and can have opposing pairs of lines in the planes of the faces perpendicular to the length of the stem 10 that are parallel to each another. The stem 10 also includes trunnion 12, which has a self-holding taper, for example, a Morse taper, and top 12T; and hole 13 tapped with screw threads.

One-piece neck 20 may be made of the aforesaid alloy, and can include associated generally curved mass 20A, distal base 20B, and cervix 20C, which can be considered to be on an upper portion of the neck 20 extending from the mass and can be pinched or drawn closer, opposing substantially parallel flat faces 20F, which blend into opposing flattened curved faces 20FC, with the lower one of which 20FCL curving concavely in a slight manner between the base 20B and the cervix 20C when viewed perpendicular to the faces 20F, and the upper one of which 20FCU curving convexly between the base 20B and the cervix 20C when viewed perpendicular to the faces 20F. The neck 20, in addition, has lower female receptacle 22 opening with respect to the base 20B, which has a self-holding taper for the trunnion 12, for example, of a corresponding Morse taper; may have upper access opening 23 to the receptacle 22, which may have a conical upper wall; and has ball-mating, trunnion 24 projecting from the cervix 20C, which has a self-holding taper, for example, a Morse taper. Securing screw 30, which also may be made of the aforesaid alloy, with truncated inverse cone head, may pass through the access opening 23 to thread in the tapped hole 13. Ball head 40, for instance, of ceramic, say, a magnesium oxide stabilized tetragonally toughened zirconia, or a metal, with a female self-holding tapered receptacle 44, for example, of a corresponding Morse taper, completes the component 100. A kit may be provided, and it may provide, for example, mix and match capability of various sizes of stem(s) 10 and neck(s) 20; stem(s) 10, neck(s) 20 and securing screw(s) 30; stem(s) 10, neck(s) 20 and head(s) 40; or stem(s) 10, neck(s) 20, securing screw(s) 30 and head(s) 40.

Some dimensions, which can be taken as approximate, of an exemplary embodiment of the component 100 are listed as follows:

Overall length of the stem 10: 5⅞ inches (14.9 cm)
Length from shoulder 11S to tip 11T: 4⅞ inches (12.4 cm)
Width by shoulder 11S between rounded faces 11R: ¾ inch (1.9 cm)
Width before rounded tip 11T between rounded faces 11R: ⅜ inch (1 cm)
Width by shoulder 11S between flat faces 11F: ½ inch (1.3 cm)
Width by rounded tip 11T between flat faces 11F: ¼ inch (0.6 cm)
Greatest distance of the neck 10 between base 10B and trunnion 24: 3 5/16 inch (8.4 cm)
Width between the curved faces 20FCL, 20FCU, near center: 1 inch (2.5 cm)
Width between flat faces 20F: ⅝ inch (1.6 cm)
Overall length of the screw 30: 11/16 inch (1.7 cm)
Length of its threaded portion: ⅜ inch (1 cm)
Greatest width of screw head: 11/32 inch (0.9 cm)
Width of screw head before threads: 3/16 inch (0.5 cm).

CONCLUSION TO THE INVENTION

The present invention is thus and hereby provided. Various feature(s), part(s), step(s), subcombination(s) and/or combination(s) can be employed with or without reference to other feature(s), part(s), step(s), subcombination(s) and/or combination(s) in the practice of the invention, and numerous modifications can be effected within its spirit, the literal claim scope of which is particularly pointed out as follows:

What is claimed is:

1. A hip implant femoral component, which comprises:
(A) a hip implant femoral component stem made with a nonmagnetic cobalt-chromium-molybdenum alloy, which exhibits high strength, wear and corrosion resistance, as a wrought powder metallurgy product, is formed from a cobalt-chromium-molybdenum alloy powder, and is substantially 100% dense, wherein the stem includes a distal portion—wherein the distal portion of the stem has:
   a length, substantially throughout which two opposing substantially flat faces blend into two opposing convexly rounded faces;
   a proximal end from which the trunnion projects, wherein the proximal end has a shoulder; and
   a rounded tip—
wherein:
   the flat faces are in a form of a truncated slight V-shape when viewed generally perpendicular to the rounded faces and have greater distance between them by the shoulder than by the rounded tip, and the flat faces have less distance between them about the proximal end and substantially along the length of the stem than the rounded faces correspondingly have between them;
   the stem tapers from its proximal end to its rounded tip; and
   the flat faces and the rounded faces, respectively, are symmetrical about a central axis; and
(B) a neck also made of a nonmagnetic cobalt-chromium-molybdenum alloy, which exhibits high strength, wear and corrosion resistance, as a wrought powder metallurgy product, is formed from a cobalt-chromium-molybdenum alloy powder, and is substantially 100% dense, wherein:
   the neck is attached to the stem trunnion of the stem;
   the neck includes an associated generally curved mass having a distal base, an upper pinched cervix, a lower curved face curving concavely with respect to and between the distal base and the upper pinched cervix, and an upper curved face curving convexly with respect to and between the distal base and the upper pinched cervix; a lower female receptacle opening with respect to the distal base, which has a self-holding taper for receiving the trunnion of the stem; and a ball-mating, neck trunnion projecting from and in a direction substantially coaxial with the pinched cervix, which has a self-holding taper that is useful for holding a hip ball head with a corresponding self-holding tapered receptacle; and
   the neck and the neck trunnion together are of one piece.

2. The hip implant femoral component of claim 1, wherein:
   the alloy of the hip implant femoral component stem has a composition in weight percent of about the following: Carbon, 0.35% max.; Manganese, 1.00% max.; Silicon, 1.00% max.; Chromium, 26.0%-30.0%; Molybdenum, 5.0%-7.0%; Nickel, 3.00% max.; Nitrogen, 0.25% max.; Iron, 1.00% max.; Oxide Forming Metals, 0.01% max.; Cobalt, balance; wherein the amounts of carbon and nitrogen in the alloy satisfy the relationship: $62.866 + 360{,}93 \times (\% \text{ Carbon}) + 286{,}633 \times (\% \text{ Nitrogen}) - 682.165 \times (\% \text{ Carbon})^2 - 641.702 \times (\% \text{ Nitrogen})^2$ is greater than or equal to 120—and is substantially 100% dense; and
   the alloy of the neck also has a composition in weight percent of about the following: Carbon, 0.35% max.; Manganese, 1.00% max.; Silicon, 1.00% max.; Chromium, 26.0%-30.0%; Molybdenum, 5.0%-7.0%; Nickel, 3.00% max.; Nitrogen, 0.25% max.; Iron, 1.00% max.; Oxide Forming Metals, 0.01% max.; Cobalt, balance; wherein the amounts of carbon and nitrogen in the alloy satisfy the relationship: $62.866 + 360.93 \times (\% \text{ Carbon}) + 286,633 \times (\% \text{ Nitrogen}) - 682.165 \times (\% \text{ Carbon})^2 - 641.702 \times (\% \text{ Nitrogen})^2$ is greater than or equal to 120—and is substantially 100% dense.

3. The hip implant femoral component of claim 2, which further comprises the hip ball head attached to the neck trunnion of the neck.

4. The hip implant femoral component of claim 1, which further comprises the hip ball head attached to the neck trunnion of the neck.

5. A hip implant femoral component, which comprises:
(A) a hip implant femoral component stem, wherein the stem includes a distal portion having a length, substantially throughout which two opposing substantially flat faces blend into two opposing convexly rounded faces; a proximal end; a stem trunnion projecting from the proximal end, which has a self-holding taper and a top, and which projects from and in a direction substantially coaxial with the distal portion; a hole in the stem trunnion tapped with screw threads, with the hole having an opening in the top of and substantially coaxial with the stem trunnion; and a rounded tip—wherein the stem and the stem trunnion together are of one piece; wherein:
the flat faces are a in form of a truncated slight V-shape when viewed generally perpendicular to the rounded faces and have greater distance between them by a shoulder than by by the rounded tip, and the flat faces have less distance between them about the proximal end and substantially along the length of the stem than the rounded faces correspondingly have between them; and
the stem tapers from the proximal end to the rounded tip;
(B) a neck attached to the stem trunnion of the stem, with the neck including an associated generally curved mass having a distal base, an upper pinched cervix, two opposing substantially parallel flat faces that blend into opposing flattened curved faces, lower and upper, with the lower flattened curved face curving concavely between the distal base and the upper pinched cervix when viewed perpendicular to the two flat faces of the neck, and an upper flattened curved face curving convexly between the distal base and the upper pinched cervix when viewed perpendicular to the two flat faces of the neck; a neck trunnion projecting from and in a direction substantially coaxial with the pinched cervix, which has a self-holding taper that is useful for holding a hip ball head with a corresponding self-holding tapered receptacle; a lower female receptacle opening with respect to the distal base, which has a self-holding taper for receiving the male stem trunnion of the stem; at least one upper access opening to the receptacle of neck; and the neck and the neck trunnion together are of one piece; and
(C) a securing screw threaded into the hole in the stem trunnion of the stem—wherein the securing screw is of one piece.

6. The hip implant femoral component of claim 5, wherein the securing screw has an inversely conical head.

7. The hip implant femoral component of claim 5, which further comprises the hip ball head attached to the neck trunnion of the neck.

8. The hip implant femoral component of claim 7, wherein the stem is made with a nonmagnetic cobalt-chromium-molybdenum alloy, which exhibits high strength, wear and corrosion resistance, as a wrought powder metallurgy product, is formed from a cobalt-chromium-molybdenum alloy powder having a composition in weight percent of about the following: Carbon, 0.35% max.; Manganese, 1.00% max.; Silicon, 1.00% max.; Chromium, 26.0%-30.0%; Molybdenum, 5.0%-7.0%; Nickel, 3.00% max.; Nitrogen, 0.25% max.; Iron, 1.00% max.; Oxide Forming Metals, 0.01% max.; Cobalt, balance; wherein the amounts of carbon and nitrogen in the alloy satisfy the relationship: $62.866 + 360.93 \times (\% \text{ Carbon}) + 286,633 \times (\% \text{ Nitrogen}) - 682.165 \times (\% \text{ Carbon})^2 - 641.702 \times (\% \text{ Nitrogen})^2$ is greater than or equal to 120—and is substantially 100% dense.

9. The hip implant femoral component of claim 5, wherein:
the stem is made with a nonmagnetic cobalt-chromium-molybdenum alloy, which exhibits high strength, wear and corrosion resistance, as a wrought powder metallurgy product, is formed from a cobalt-chromium-molybdenum alloy powder having a composition in weight percent of about the following: Carbon, 0.35% max.; Manganese, 1.00% max.; Silicon, 1.00% max.; Chromium, 26.0%-30.0%; Molybdenum, 5.0%-7.0%; Nickel, 3.00% max.; Nitrogen, 0.25% max.; Iron, 1.00% max.; Oxide Forming Metals, 0.01% max.; Cobalt, balance; wherein the amounts of carbon and nitrogen in the alloy satisfy the relationship: $62.866 + 360.93 \times (\% \text{ Carbon}) + 286,633 \times (\% \text{ Nitrogen}) - 682.165 \times (\% \text{ Carbon})^2 - 641.702 \times (\% \text{ Nitrogen})^2$ is greater than or equal to 120—and is substantially 100% dense; and
the neck is also made with a nonmagnetic cobalt-chromium-molybdenum alloy, which exhibits high strength, wear and corrosion resistance, as a wrought powder metallurgy product, is formed from a cobalt-chromium-molybdenum alloy powder having a composition in weight percent of about the following: Carbon, 0.35% max.; Manganese, 1.00% max.; Silicon, 1.00% max.; Chromium, 26.0%-30.0%; Molybdenum, 5.0%-7.0%; Nickel, 3.00% max.; Nitrogen, 0.25% max.; Iron, 1.00% max.; Oxide Forming Metals, 0.01% max.; Cobalt, balance; wherein the amounts of carbon and nitrogen in the alloy satisfy the relationship: $62.866 + 360.93 \times (\% \text{ Carbon}) + 286,633 \times (\% \text{ Nitrogen}) - 682.165 \times (\% \text{ Carbon})^2 - 641.702 \times (\% \text{ Nitrogen})^2$ is greater than or equal to 120—and is substantially 100% dense.

10. The hip implant femoral component of claim 9, wherein the securing screw is also made with a nonmagnetic cobalt-chromium-molybdenum alloy, which exhibits high strength, wear and corrosion resistance, as a wrought powder metallurgy product, is formed from a cobalt-chromium-molybdenum alloy powder having a composition in weight percent of about the following: Carbon, 0.35% max.; Manganese, 1.00% max.; Silicon, 1.00% max.; Chromium, 26.0%-30.0%; Molybdenum, 5.0%-7.0%; Nickel, 3.00% max.; Nitrogen, 0.25% max.; Iron, 1.00% max.; Oxide Forming Metals, 0.01% max.; Cobalt, balance; wherein the amounts of carbon and nitrogen in the alloy satisfy the relationship: $62.866 + 360.93 \times (\% \text{ Carbon}) + 286,633 \times (\% \text{ Nitrogen}) - 682.165 \times (\% \text{ Carbon})^2 - 641.702 \times (\% \text{ Nitrogen})^2$ is greater than or equal to 120—and is substantially 100% dense.

11. The hip implant femoral component of claim 10, wherein the securing screw has an inversely conical head.

12. The hip implant femoral component of claim 11, wherein the stem, neck, and securing screw are made with essentially the same alloy.

13. The hip implant femoral component of claim 10, wherein the stem, neck, and securing screw are made with essentially the same alloy.

14. The hip implant femoral component of claim 9, wherein the stem and neck are made with essentially the same alloy.

15. A kit comprising:
(A) a hip implant femoral component stem made with a nonmagnetic cobalt-chromium-molybdenum alloy, which exhibits high strength, wear and corrosion resistance, as a wrought powder metallurgy product, is formed from a cobalt-chromium-molybdenum alloy powder having a composition type analysis in weight percent of about the following: Carbon, 0.20%-0.30%; Chromium, 26.00%-30.00%; Molybdenum, 5.00%-7.00%; Nitrogen, 0.15%-0.20%; Cobalt, balance–and is substantially 100% dense, wherein the stem includes:
a distal portion; and
a stem trunnion having a self-holding taper and a top, which projects from and in a direction substantially coaxial with the distal portion—
wherein the stem and the stem trunnion together are of one piece;
(B) a neck that can be attached to the stem trunnion of the stem and also made of a nonmagnetic cobalt-chromium-molybdenum alloy, which exhibits high strength, wear and corrosion resistance, as a wrought powder metallurgy product, formed from a cobalt-chromium-molybdenum alloy powder having a composition type analysis in weight percent of about the following: Carbon, 0.20%-0.30%; Chromium, 26.00%-30.00%; Molybdenum, 5.00%-7.00%; Nitrogen, 0.15%-0.20%; Cobalt, balance–and is substantially 100% dense, wherein:
the neck includes an associated generally curved mass having a distal base, an upper pinched cervix, a lower curved face curving concavely with respect to and between the distal base and the upper pinched cervix, and an upper curved face curving convexly with respect to and between the distal base and the upper pinched cervix; a lower female receptacle opening with respect to the distal base, which has a self-holding taper for receiving the trunnion of the stem; and a ball-mating, neck trunnion projecting from and in a direction substantially coaxial with the pinched cervix, which has a self-holding taper that is useful for holding a hip ball head with a corresponding self-holding tapered receptacle; and
the neck and the neck trunnion together are of one piece; and
(C) the hip ball head with the self-holding tapered receptacle.

16. The kit of claim 15, wherein the stem trunnion of the stem has a hole, which is tapped with screw threads, with the hole having an opening in the top of an substantially coaxial with the stem trunnion; the neck includes at least one upper access opening through which a securing screw can be passed for threading into the hole of the stem trunnion of the stem; and the securing screw is also provided, wherein the securing screw has a truncated inverse cone head and is of one piece.

17. A hip implant femoral component, which comprises a hip implant femoral component neck, which is attachable to a hip implant femoral component stem, wherein:
the stem includes a distal portion having a length and a tip; a proximal end; a stem trunnion projecting from the proximal end, which has a self-holding taper and a top; and
the neck includes an associated generally curved mass having a distal base, an upper pinched cervix, a lower curved face curving concavely with respect to said mass from the distal base to the upper pinched cervix, and an upper curved face curving convexly with respect to said mass from the distal base to the upper pinched cervix; a lower female receptacle opening with respect to the distal base, which has a self-holding taper for receiving the trunnion of the stem; and a ball-mating, neck trunnion projecting from and in a direction substantially coaxial with the pinched cervix, which has a self-holding taper that is useful for holding a hip ball head with a corresponding self-holding tapered receptacle; and the neck and the neck trunnion together are of one piece.

18. The hip implant femoral component of claim 17, wherein the neck is made with a nonmagnetic cobalt-chromium-molybdenum alloy, which exhibits high strength, wear and corrosion resistance, as a wrought powder metallurgy product, is formed from a cobalt-chromium-molybdenum alloy powder having a composition in weight percent of about the following: Carbon, 0.35% max.; Manganese, 1.00% max.; Silicon, 1.00% max.; Chromium, 26.0%-30.0%; Molybdenum, 5.0%-7.0%; Nickel, 3.00% max.; Nitrogen, 0.25% max.; Iron, 1.00% max.; Oxide Forming Metals, 0.01% max.; Cobalt, balance; wherein the amounts of carbon and nitrogen in the alloy satisfy the relationship: $62.866 + 360.93 \times (\% \text{ Carbon}) + 286{,}633 \times (\% \text{ Nitrogen}) - 682.165 \times (\% \text{ Carbon})^2 - 641.702 \times (\% \text{ Nitrogen})^2$ is greater than or equal to 120—and is substantially 100% dense.

19. The hip implant femoral component of claim 17, which further comprises the stem and the ball head, wherein the neck is attached to the stem, and the ball head is attached to the neck.

20. The hip implant femoral component of claim 19, which further comprises a securing screw, wherein:
the stem trunnion has a hole tapped with screw threads, with the hole having an opening in the top of and substantially coaxial with the stem trunnion;
the neck has at least one upper access opening to the lower female receptacle opening; and
the securing screw is threaded through the at least one upper access opening into the hole in the stem trunnion.

* * * * *